United States Patent
Ellis

(10) Patent No.: US 10,092,341 B2
(45) Date of Patent: Oct. 9, 2018

(54) SCREW

(71) Applicant: LMM IP Holding Pty Ltd., Port Macquarie (AU)

(72) Inventor: Liam Patrick Ellis, Blackalls Park (AU)

(73) Assignee: LMM IP HOLDINGS PTY LTD, Port MacQuarie (AU)

( * ) Notice: Subject to any disclaimer, the term of this patent is extended or adjusted under 35 U.S.C. 154(b) by 570 days.

(21) Appl. No.: 14/434,384

(22) PCT Filed: Sep. 25, 2013

(86) PCT No.: PCT/AU2013/001100
§ 371 (c)(1),
(2) Date: Apr. 8, 2015

(87) PCT Pub. No.: WO2014/056017
PCT Pub. Date: Apr. 17, 2014

(65) Prior Publication Data
US 2015/0230844 A1 Aug. 20, 2015

(30) Foreign Application Priority Data
Oct. 9, 2012 (AU) .............................. 2012904413

(51) Int. Cl.
*A61B 17/86* (2006.01)
(52) U.S. Cl.
CPC ........ *A61B 17/8635* (2013.01); *A61B 17/863* (2013.01); *A61B 17/8625* (2013.01); *A61B 2017/8655* (2013.01)

(58) Field of Classification Search
CPC ... A61B 17/86; A61B 17/8625; A61B 17/863; A61B 17/8635; A61B 17/864;
(Continued)

(56) References Cited

U.S. PATENT DOCUMENTS 4,069,730 A * 1/1978 Gutshall ............. F16B 25/0021
411/386
4,537,185 A 8/1985 Stednitz
(Continued)

FOREIGN PATENT DOCUMENTS

WO WO 2010/054720 5/2010

OTHER PUBLICATIONS

International Search Report re International Application No. PCT/AU2013/001100 dated Oct. 29, 2013, in 3 pages.

*Primary Examiner* — Kevin T Truong
*Assistant Examiner* — Tracy Kamikawa
(74) *Attorney, Agent, or Firm* — Knobbe Martens Olson and Bear LLP

(57) ABSTRACT

A screw has a screw tip defined at a forward end of the screw. A screw head is formed at a rear end of the screw. A screw thread helically extends from adjacent the screw tip towards the screw head. The screw thread has a series of successive screw thread portions each helically extending through 360 degrees. At least one flute extends from adjacent the screw tip towards the screw head through at least one of the screw thread portions. For each flute, a leading edge region of each of at least one screw thread portion through which the flute extends is convexly curved. Each leading edge region is defined by a trailing wall of the flute adjacent a crest of the respective screw thread portion.

11 Claims, 4 Drawing Sheets

(58) Field of Classification Search
CPC ............ A61B 17/866; A61B 2017/8655; F16B 25/0015; F16B 25/0036; F16B 25/0042; F16B 25/0052; F16B 25/0057; F16B 25/0063; F16B 25/0078; F16B 25/0084; F16B 25/106

See application file for complete search history.

(56) References Cited

U.S. PATENT DOCUMENTS

| | | | |
|---|---|---|---|
| 6,565,573 B1 * | 5/2003 | Ferrante | A61B 17/863 606/308 |
| 7,108,607 B2 * | 9/2006 | Swim, Jr. | F16B 35/041 470/185 |
| 2005/0135897 A1 | 6/2005 | Swim | |

* cited by examiner

SCREW

FIELD

The field of the invention relates to a screw and in particular relates to, but is not limited to, a bone screw.

BACKGROUND

Bone screws are regularly utilised in orthopaedic surgery for the fixation of fractured bone fragments and the like.

One common form of bone screw is a self-tapping bone screw having a screw thread that cuts into bone material forming the wall of a pre-drilled hole extending through the bone fragments to be fixed. This cutting action of the screw thread creates an internal thread in the bone, along which the bone screw thread is advanced, with engagement between the (external) screw thread and the internal bone thread fixing the screw within the bone fragments. The self-tapping bone screws typically have a series of flutes or grooves extending from adjacent the screw tip towards the screw head, creating discontinuities in the otherwise continuous bone screw thread so as to define discrete screw thread segments. The sharp leading edge of each of these thread segments, defined at the intersection between the crest of the thread segment and the trailing wall of the adjacent flute provides the cutting action of the thread.

The amount of fixation that the screw thread provides in the bone is dependent upon a number of variables. These variables include the thread surface area and volume of the interface between the external screw thread and internal bone thread, the number of full revolution thread portions engaged for each bone fragment, the friction generated between the external screw thread and internal bone thread and the quality of the bone material in which the external screw thread is engaged. The greater the number of thread portions, the greater the interface volume and the greater the friction, the greater will be the fixation and pullout strength of the bone screw. The pullout strength and fixation is, however, at times insufficient, resulting in loosening of the bone screw or backing out of the bone post-operatively.

OBJECT OF THE INVENTION

It is an object of the present invention to substantially overcome or at least ameliorate the above problem.

SUMMARY OF INVENTION

The present invention provides a screw having a longitudinal axis and comprising:
  a screw tip defined at a forward end of said screw;
  a screw head formed at a rear end of said screw;
  a screw thread helically extending from adjacent said screw tip towards said screw head, said screw thread having a series of successive screw thread portions each helically extending through 360 degrees; and
  at least one flute extending from adjacent said screw tip towards said screw head through at least one of said screw thread portions,
  wherein, for each said flute, a leading edge region of each of at least one said screw thread portion through which said flute extends is convexly curved, each said leading edge region being defined by a trailing wall of said flute adjacent a crest of the respective said screw thread portion.

In a preferred form, for each said flute, said leading edge region of at least the forwardmost (and preferably at least the three forwardmost) screw thread portion is convexly curved.

Typically, each convexly curved said leading edge region has a radius of at least 0.05 mm, more typically at least 0.1 mm.

In a preferred form each convexly curved said leading edge region has a radius of approximately 0.4 mm.

Typically, for each said flute, a trailing edge region of each of at least one said screw thread portion through which said flute extends is convexly curved, each said trailing edge region being defined by a leading wall of said flute adjacent said crest of the respective said screw thread portion.

In a preferred form, for each said flute, said trailing edge region of at least three screw thread portions is convexly curved.

Typically, each convexly curved said trailing edge region has a radius of at least 0.05 mm, more typically at least 0.1 mm.

In a preferred form, each convexly curved said trailing edge region has a radius of approximately 1.0 mm.

In a preferred form, said screw has three said flutes radially spaced about said longitudinal axis.

Typically, said screw is a bone screw.

In the context of the present specification, the terms "leading" and "trailing" are used to indicate features of the screw that lead or trail, respectively, as the screw rotates in the intended manner during insertion of the screw.

DESCRIPTION OF EMBODIMENTS

Figure 1:
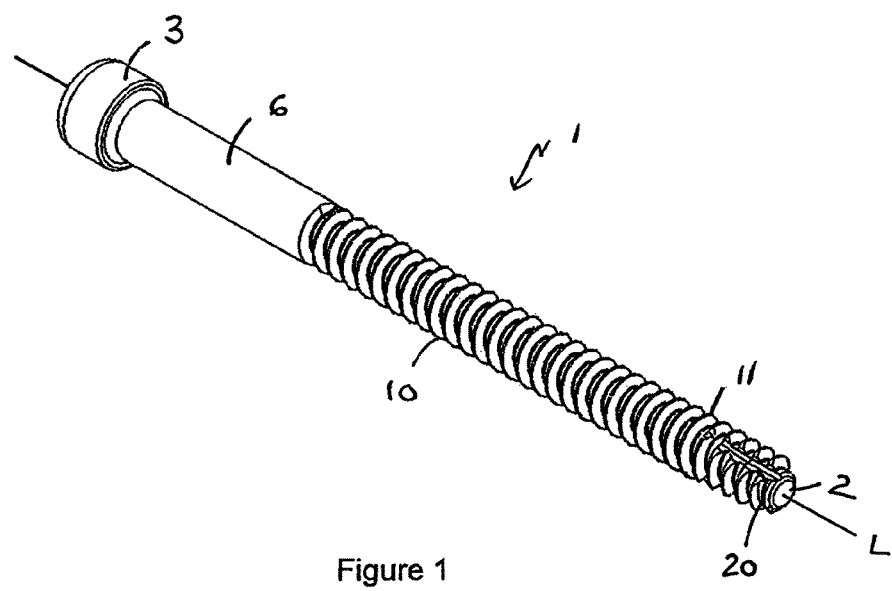
FIG. 1 is a front perspective view of a screw.
Figure 2:
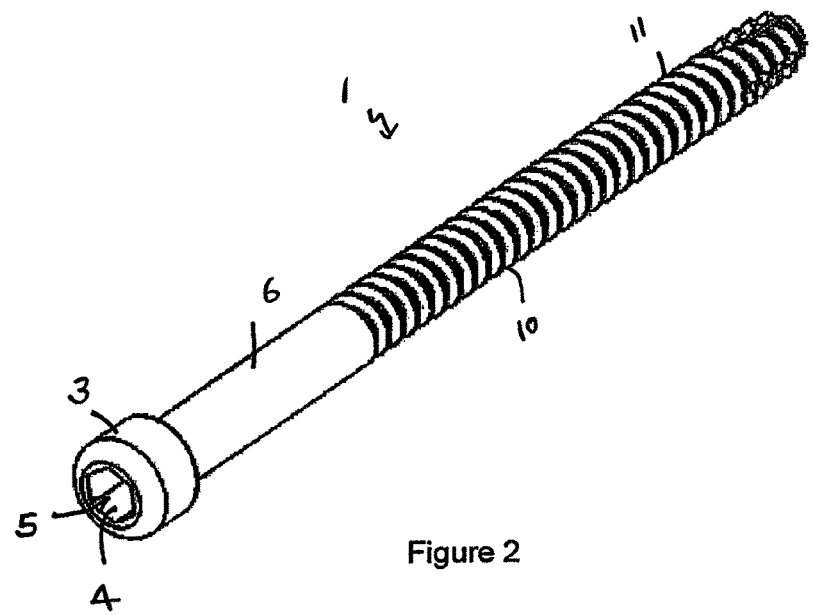
FIG. 2 is rear perspective view of the screw of FIG. 1.
Figure 3:
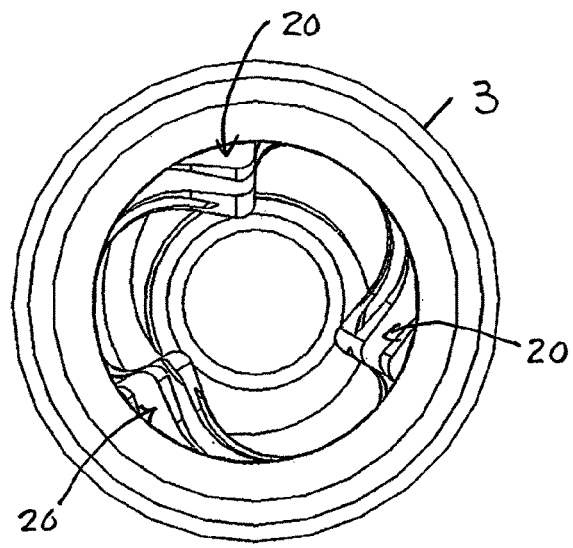
FIG. 3 is front end view of the screw of FIG. 1.

Referring to FIGS. 1 to 6 of the accompanying drawings, a screw 1, which is here in the form of a bone screw, extends along a central longitudinal axis L. The screw 1 has a screw tip 2 at a forward end of the screw 1 and a screw head 3 formed at a rear end of the screw 1. The screw head 3 has a plurality of drive surfaces 4 for rotatably driving the screw 1. In the arrangement depicted as best seen in FIG. 2, the drive surfaces 4 are internal surfaces of a drive socket 5 configured to receive an allan key type driver. The screw head 3 may otherwise be configured in any known manner including with the provision of external drive surfaces for engaging a drive socket, or one or more slots for engaging a screwdriver blade or blades. The screw tip 2 is here blunt, having a convex rounded form. It is also envisaged, however, that the screw tip 2 may be of any other known form, including a sharp tip.

The screw 1 further comprises a screw thread 10 helically extending about the longitudinal axis L from adjacent the screw tip 2 towards the screw head 3. In the particular configuration depicted, the screw thread 10 only extends partway along the length of the screw 1, leaving an unthreaded shank 6 between the screw thread 10 and screw head 3. The screw thread 10 has a series of successive screw thread portions 11, that each helically extends through 360 degrees. (i.e., a full revolution) about the longitudinal axis L. At any given point about the longitudinal axis L, the centre of successive thread portions 11 are spaced by what is referred to as the pitch of the screw thread 10. Each thread portion 11 referred to herein is often colloquially referred to as a separate thread although, in fact, the thread is continuous and in the arrangement depicted a single screw thread 10 extends helically about the longitudinal axis L along the full length of the thread. With the screw thread 10 comprising a single thread, the thread pitch is equal to the thread lead, although it is envisaged that the screw 1 may be either double-threaded or triple-threaded, so that the thread lead is either two times or three times the thread pitch.

Figure 4:
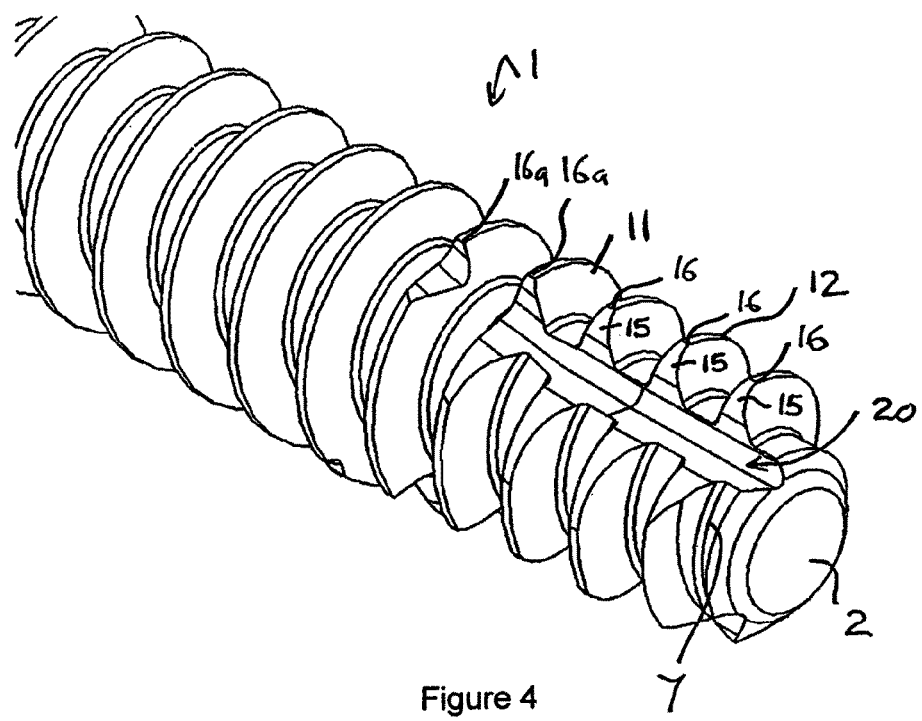
FIG. 4 is an enlarged fragmentary perspective view of the screw of FIG. 1.

At least one flute 20 extends from adjacent the screw tip 2 towards the screw head 3. In the arrangement depicted, three flutes 20 are provided, equidistantly spaced radially about the longitudinal axis L. Each flute extends through at least one of the screw thread portions 11. As best shown in FIG. 4, in the arrangement depicted, each flute 20 extends through between four and six thread portions 11. Each of the flutes 20 would typically be formed in the screw 1 by way of a grinding wheel after formation of the screw thread 10. In at least the preferred embodiment, the depth of each flute 20 decreases towards the rear end of the flute 20 (i.e., towards the screw head 3), with the flute 20 impinging on the core 7 of the screw 1 adjacent the screw tip 2 and reducing in depth such that it gradually runs out as it passes rearwardly through subsequent screw thread portions 11. In at least a preferred embodiment, the forward end region of each flute 20, adjacent the screw tip 2, extends substantially parallel to the longitudinal axis L whilst the rear end region of the flute 20 wraps around the longitudinal axis L in a clockwise direction as viewed from the screw tip 2. The screw 1 depicted has a right-handed thread, such that it is intended to be inserted by rotating in a clockwise direction as viewed from the rear (i.e., from the screw head 3). Left hand threads are also envisaged.

Throughout this specification, various features of the screw 1 will be referred to as "leading" or "trailing" with this terminology indicating features that lead or trail respectively as the screw 1 rotates in the intended direction during insertion/advancement of the screw. For a right-handed thread, as noted above, this intended direction is a clockwise direction as viewed from the rear.

Figure 5:
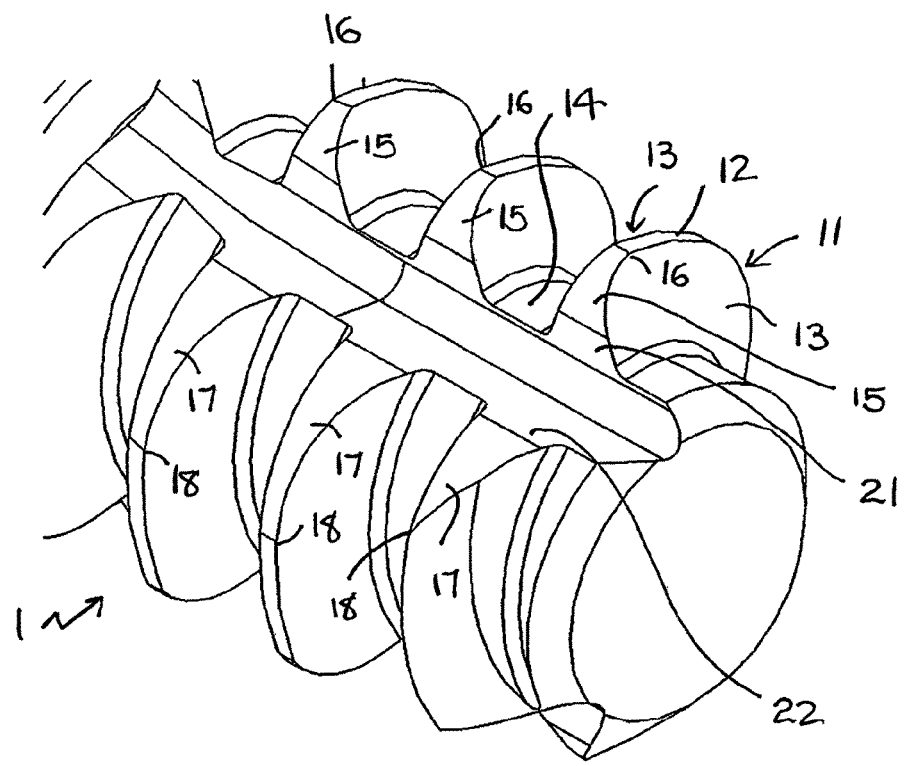
FIG. 5 is a further enlarged fragmentary perspective view of the screw of FIG. 1.
Figure 6:
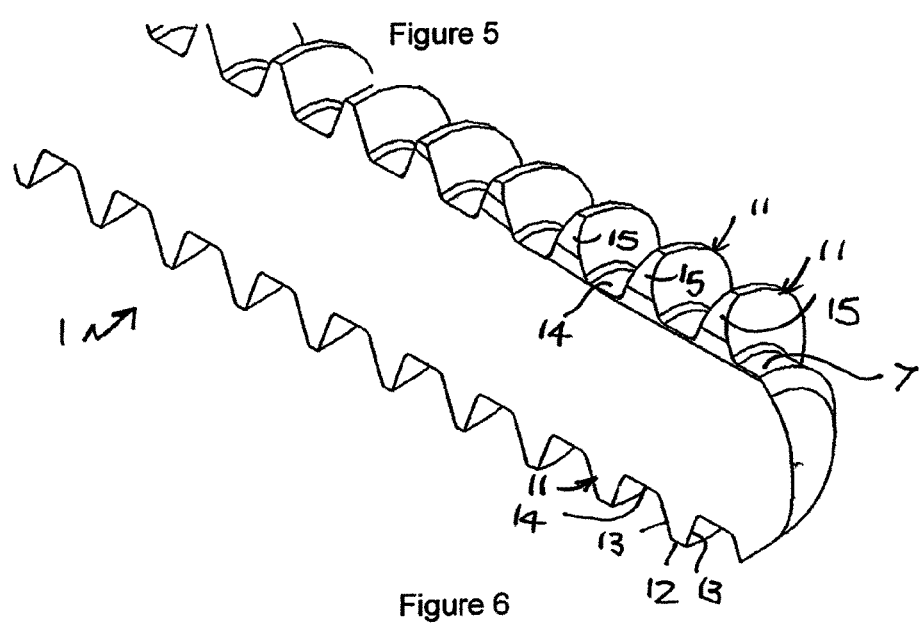
FIG. 6 is a longitudinally cross-sectional view of the screw of FIG. 1.

Referring to FIG. 5 each of the screw thread portions 11 is defined by a crest 12 (otherwise known as an apex) forming the radially outermost surface of the thread portion 11 at the major diameter of the screw 1 and a pair of opposing flanks 13 (otherwise known as sides) of the thread that are mutually inclined by what is referred to as the thread angle. The individual screw thread portions 11 are each separated by a thread root 14, being the surface of the screw thread 10 located at the minor diameter of the screw 1.

Each of the flutes 20 provides a discontinuity in each of the screw thread portions 11 through which it extends, with the trailing wall 21 of each of the flutes 20 defining a leading edge region 15 of each screw thread portion 11 adjacent the crest 12 of the screw thread portion 11. With a typical fluted self-tapping screw, this leading edge region defines with the crest a sharp cutting edge for tapping an internal thread in the material in which the screw is to be implanted. Here the leading edge region 15, of at least one of the thread portions 11 through which the flute 20 extends, typically including at least the forwardmost (and more typically at least the three fowardmost) screw thread portion 11, is convexly curved. As can be best appreciated from FIG. 5, this avoids a sharp cutting edge at the leading end of the crest 12 for at least the forwardmost three screw thread portions 11 in the arrangement depicted, with a soft transition edge 16 being defined between the crest 12 and leading edge region 15. Referring to FIG. 4, for the rearwardmost one or two screw thread portions 11 through which the flutes 20 extend, in the runout region of the flutes 20 where the depth of the flutes 20 decreases towards zero, the particular configuration of the grinding wheel used results in a relatively flat portion of the side of the grinding wheel creating a relatively flat leading edge region 15 and, accordingly, at least a relatively sharp edge 16a formed at the intersection between the crest 12 and leading edge region 15.

The effect of the convexly curved leading edge regions 15 is for the screw thread portions 11 to elastically deform the elastic bone material within which the screw 1 is intended to be inserted, rather than cutting an internal thread in the bone material that matches the external thread 10 of the screw 1. The screw thread 10 thus compresses the bone material to form a smooth helical gully along the path of the screw thread 10, rather than a sharp thread cut into the bone material. By the time the rearwardmost thread portions 11 that define sharp edges 16a discussed above engage the bone material, the forwardmost screw thread portions 11 will have already elastically deformed the bone material such that the sharp edges 16a will still not act to cut any significant thread into the bone material. By elastically deforming the bone material, rather than cutting a mating thread through the bone material, an enhanced compression load between the crests 12 (and flanks 13) of the screw thread portions 11 and the internal wall of the bone material, may be achieved, thereby providing an increased frictional force which tends to retain the screw 1 within the bone material, thereby tending to reduce the possibility of the screw 1 loosening or backing out of the bone.

It is preferred that the radius of the convexly curved leading edge region 15, for at least some of the screw thread portions 11, particularly the forwardmost (and more preferably at least three forwardmost) screw thread portion 11, has a radius of at least 0.05 mm, more preferably at least 0.1 mm and more typically at least 0.2 mm. In the particular arrangement depicted, the leading edge region 15 of at least the three forwardmost screw thread portions 11, for each flute 20, is approximately 0.4 mm.

As will also be appreciated by a person skilled in the art, the radius of each convexly curved leading edge region 15 may well vary, however, it is preferred that at all points along each convexly curved leading edge region 15 have a radius of at least 0.05 mm, more preferably at least 0.1 mm and more typically at least 0.2 mm.

The leading wall 22 of each of the flutes 20 defines a trailing edge region 17 of each screw thread portion 11 adjacent the crest 12 of the screw thread portion 11. With a typical self-tapping screw, this trailing edge region defines with the crest a sharp cutting edge. Here, however, the trailing edge region 17 of at least one of the screw thread portions 11 through which the flute 20 extends, typically including at least the forwardmost (and preferably at least three forwardmost) screw thread portion 11, is convexly curved. As can again best be appreciated from FIG. 5 this avoids a sharp cutting edge at the trailing end of the crest 12 for at least the forwardmost four screw thread portions 11 in the arrangement depicted, providing a soft transition edge 18 between the crest 12 and trailing edge region 17. As with the leading edge regions 15 of the rearwardmost screw thread portion 11 through which the flutes 20 extend, a relatively sharp edge 18a is formed at the intersection between the crest 12 and trailing edge region 18, of the rearmost screw thread portions at the rear runout of each flute 20.

The effect of the convexly curved trailing edge regions 18 is to at least substantially avoid the cutting of an internal thread in the bone material if and when the screw 1 is driven in a counter-clockwise direction to draw it out of the bone material.

It is preferred that the radius of the convexly curved trailing edge region 17, or of at least some of the screw thread portions 11, has a radius of at least 0.05 mm, more preferably at least 0.1 mm and more typically at least 0.2 mm. In the particular arrangement depicted, the trailing edge region 18 at least before the three forwardmost screw thread portions 11, for each flute 20, is approximately 1.0 mm. As with the convexly curved leading edge regions 15, the radius of each convexly curved trailing edge region 17 may well vary. It is preferred that at all points along each convexly curved trailing edge region 15 have a radius of at least 0.05 mm, more preferably at least 0.1 mm and more typically at least 0.2 mm.

Whilst, with the convexly curved configuration of the leading and trailing edge regions 15, 17, the flute 20 does not serve to provide a self-tapping function of the screw 1 as is the case with typical fluted self-tapping screws, the flutes 20 are still beneficial in that they provide discontinuities in the screw thread portions 11, making it easier to commence insertion of the screw 1 into a hole pre-drilled into bone material (or other material as desired) providing a reduced frictional resistance to rotational driving of the screw 1 than would be experienced if the forwardmost screw thread portions were continuous, requiring elastic deformation of the bone material along the entire circumferential length of each screw thread portion 11. Provision of the flutes 20 and convexly curved leading edge portions 15 also provides multiple starting points or leads for forming the deformed helical gully in the bone material for passage of the screw thread portions 11.

The dimensional characteristics of the screw 1, including of the screw thread 10 may be selected to suit specific applications utilising normal principles. For typical bone screw applications, the major diameter of the screw 1 may suitably be of the order of 5.0 mm, with a minor diameter of the order of 4.0 to 4.2 mm, providing a thread height of the order of 0.4 to 0.5 mm. The thread pitch may typically be of the order of 1.0 to 1.75 mm, whilst the thread angle may suitably be of the order of 35 to 60 degrees as desired. In the configuration depicted, the thread crest 12 has a width of approximately 0.1 mm, and the thread root 14 has a width of approximately 0.5 mm. In the configuration depicted, the intersection between the crest 12 and each flank 13 of the thread 10 is a sharp edge, although it is envisaged that this intersection may be convexly curved.

Figure 7:
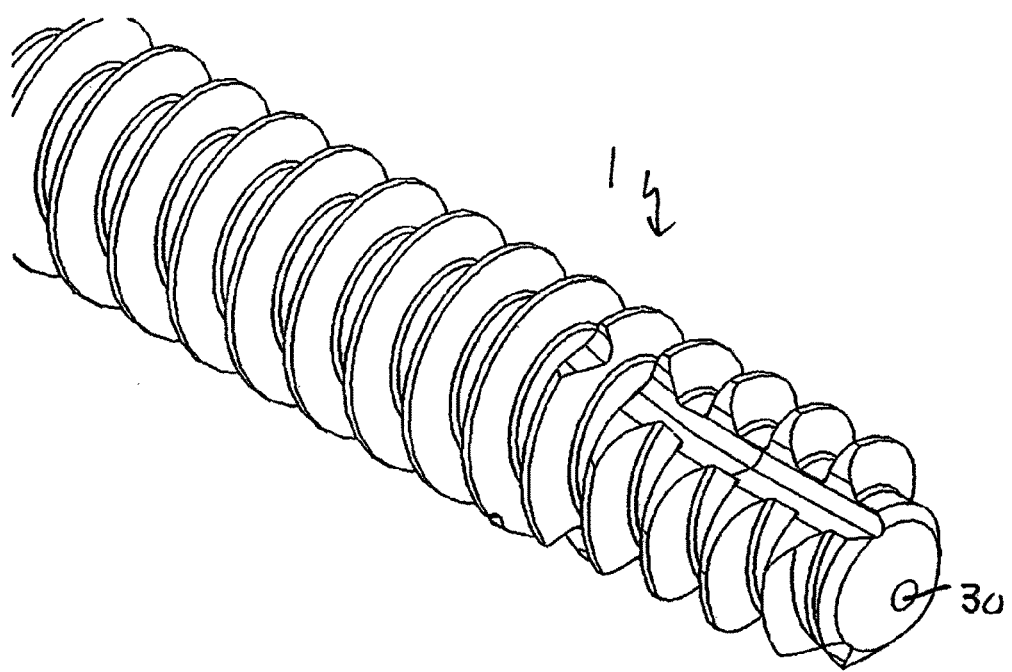
FIG. 7 is a fragmentary enlarged perspective view of a modified form of screw.

Whilst the screw 1 depicted in FIGS. 1 to 6 is a form of a solid bone screw, it is also envisaged that the screw 1 may be cannulated as per the screw 1' depicted in FIG. 7, with a cannula 30 extending along the longitudinal axis L. All the features of the screw 1' are otherwise identical to that of the screw 1 described above in relation to FIGS. 1 to 6.

Whilst the screws 1, 1' above have been described in relation to a bone screw, it is also envisaged that the principles described will be equally applicable to other forms of screw configured to be inserted into other elastically flexible materials such as plastics materials.

The invention claimed is:

1. A screw having a longitudinal axis and comprising:
a screw tip defined at a forward end of said screw;
a screw head formed at a rear end of said screw;
a screw thread helically extending from adjacent said screw tip towards said screw head, said screw thread having a series of successive screw thread portions; and
at least one flute extending from adjacent said screw tip towards said screw head through at least one of said screw thread portions, walls of each said flute extending through the at least one of said screw thread portions, wherein each of the at least one of said screw thread portions comprises a leading edge surface connecting a crest of the respective one of said screw thread portions to one of the walls of a respective one of said flutes and a trailing edge surface circumferentially spaced from a respective leading edge surface and connecting the crest of the respective one of said screw thread portions to the other of the walls of the respective one of said flutes;
wherein, for each said flute, the leading edge surface and the trailing edge surface of each of the at least one of said screw thread portions through which said flute extends are convexly curved and each comprise a different radius of curvature than each other and the respective one of said screw thread portions at its respective crest, wherein the convexly curved leading edge surfaces are configured to elastically deform bone material into which the screw is configured to be inserted.

2. The screw of claim 1, wherein the at least one of said screw thread portions through which said flute extends includes a forwardmost screw thread portion.

3. The screw of claim 1, wherein the at least one of said screw thread portions through which said flute extends includes at least three forwardmost screw thread portions.

4. The screw of claim 1, wherein each convexly curved said leading edge surface has a radius of at least 0.05 mm.

5. The screw of claim 1, wherein each convexly curved said leading edge surface has a radius of at least 0.1 mm.

6. The screw of claim 1, wherein each convexly curved said leading edge surface has a radius of approximately 0.4 mm.

7. The screw of claim 1, wherein each convexly curved said trailing edge surface has a radius of at least 0.05 mm.

8. The screw of claim 1, wherein each convexly curved said trailing edge surface has a radius of at least 0.1 mm.

9. The screw of claim 1, wherein each convexly curved said trailing edge surface has a radius of approximately 1.0 mm.

10. The screw of claim 1, wherein said screw has three said flutes radially spaced about said longitudinal axis.

11. The screw of claim 1, wherein said screw is a bone screw.

* * * * *